United States Patent [19]

Kroeplien et al.

[11] Patent Number: 4,567,194
[45] Date of Patent: Jan. 28, 1986

[54] 2-ACYLIMIDAZOLE COMPOUNDS, THEIR SYNTHESIS AND USE AS MEDICINAL AGENTS

[75] Inventors: Udo Kroeplien; Joachim Rosdorfer, both of Essen, Fed. Rep. of Germany

[73] Assignee: The Coca-Cola Company, Atlanta, Ga.

[21] Appl. No.: 473,931

[22] Filed: Mar. 10, 1983

[51] Int. Cl.$^4$ ............... C07D 233/64; A61K 31/415
[52] U.S. Cl. .................................. 514/400; 548/343
[58] Field of Search ............... 548/343; 424/273 R; 514/400

[56] References Cited

U.S. PATENT DOCUMENTS 3,772,315 11/1973 Regel et al. ............... 548/343 X
4,124,766 11/1978 Paul et al. .................. 548/343 X Primary Examiner—Joseph Paul Brust
Attorney, Agent, or Firm—Kenyon & Kenyon

[57] ABSTRACT

The 2-acylimidazole compounds have an alkyl or aryl substitution at the 2-position and an alkyl, hydroxyalkyl, polyhydroxyalkyl or aryl substitution at the 4-position. They exhibit an ability to decrease in vivo leucocyte populations and are consequently useful as immunosuppressive medicinal agents for prevention of transplanted tissue rejection, treatment of leukemia and treatment of cell-mediated autoimmune disease.

25 Claims, No Drawings

2-ACYLIMIDAZOLE COMPOUNDS, THEIR SYNTHESIS AND USE AS MEDICINAL AGENTS

BACKGROUND OF THE INVENTION

1. Field of Invention

The present invention relates to compounds which act as immunosuppressive medicinal agents to reduce a high population of circulating leucocytes in animals and alleviate untoward effects produced thereby. More specifically, the 2-acylimidazole compounds which are synthesized and isolated according to the process of the present invention are useful to promote tissue transplant reception, and treat cell-mediated autoimmune disease.

Leucocytes, or white blood cells (WBC's), are blood cells which do not contain hemoglobin, and are phagocytic and immune responsive in nature. WBC's can be classified into five major groups, one of which is the lymphocyte group. A major function of the WBC's is to defend the body against invasion by foreign biological material such as bacteria and viruses. A major function of the lymphocytes, in particular, is concerned with the immune response which is the body's recognition and removal mechanism for handling foreign substances.

2. Description of the Prior Art

Depression of circulating leucocyte populations in animals has been discussed extensively in the scientific literature.

For example, in "The Chemistry and Metabolism of 4'-Deoxypyridoxine," CRC Press (1981), Library of Congress No. QP772.P9C6 Stephen P. Coburn reports that 4'-deoxypyridoxine has hematologic effects. When this compound is administered to rats at doses as low as 1 mg/kg and in conjunction with a vitamin $B_6$-deficient diet, it will produce leucopenia with lymphopenia and increased neutrophils. Atrophy of lymphoid elements in the thymus is consistently observed. After restoration of a normal diet, however, circulating lymphocytes double within two days and the cell population returns to normal within two weeks. When deoxypyridoxine is withdrawn but the deficient diet continued, the leukocyte count returns to normal but the granulocyte to lymphocyte ratio does not.

Coburn also has found that deoxypyridoxine causes a reduced vitamin $B_6$ uptake in human leucocytes and platelets. For cultured leucocytes treated with this compound, the maximum cellular concentration of pyridoxal phosphate ($B_6$) is about 37 ng per $10^8$ cells while the normal level is significantly higher. Deoxypyridoxine also causes a detectable decrease (ca. 15%) in the assimilation of the $B_6$ precursor pyridoxine into the cells even at a 1 to 1 ratio of deoxypyridoxine to pyridoxine. Similar effects on erythrocytes are also reported for a 1 to 1 ratio of deoxypyridoxine to pyridoxine.

The immune system seems to be sensitive to $B_6$ deficiency, and deoxypyidoxine appears to exhibit a cooperative effect with this aspect of $B_6$ deficiency. For example, it is known that the lymphoid system and consequently the immune system are influenced adversely by reducing or by eliminating specific nutrients and enzymatic cofactors from the diet. "*Human Vitamin $B_6$ Requirements,*" National Academy of Sciences (1978). Several studies have shown that a dietary deficiency of vitamin $B_6$ may result in an impairment of both humoral and cell-mediated immune responses.

The Coburn studies confirm cooperation of vitamin $B_6$ and deoxypyridoxine to affect the immune system. When rats are given deoxypyridoxine (0.1 mg/ml drinking water) in combination with a $B_6$-deficient diet, their total leucocyte population is reduced. Their neutrophils are somewhat increased while their lymphocytes are substantially reduced. Moreover, mixed lymphocyte response as measured by thymidine uptake is reduced 55 percent, the normal lymphocyte transfer reaction is reduced, and uridine incorporation into small lymphocytes is decreased.

Deoxypyridoxine also affects the immune response of primates, as shown by the Coburn report of paralytic poliomyelitis in an unvaccinated rhesus monkey (a very rare occurrence). For 17 days previous to exposure to poliomyelitis virus, the monkey received subcutaneous injections of 100 mg deoxypyridoxine per kilogram body weight (twice daily during the week, once on weekends) along with a $B_6$ deficient diet. Viral exposure then produced paralysis. Coburn suggests that suppression of the immune system, which would cause conditions favoring increased virulence of the virus, possibly produced the paralysis.

Reduced leucocyte populations may also be helpful for tissue transplantation. Coburn cites studies of the effect of $B_6$ deficiency on tissue transplantation. These studies show that $B_6$ deficiency either alone or combined with intraperitoneal injection of 250 or 500 mg deoxypyridoxine per day increase the survival of skin grafts in rats. Coburn concludes that the deoxypyridoxine may have potential clinical application in tissue transplantation.

Cell-mediated autoimmune disease is a debilitating condition which results when the immune system attacks normal, endogeneous tissue rather than foreign vectors. Often, substantial populations of leucocytes are found in such affected tissues and concurrent immune responses such as histamine release, lymph fluid infiltration, and leucocye migration are also present. Destruction of the affected tissue eventually occurs. The inability of the immune system to distinguish foreign from endogeneous tissue may be based, at least in part, upon stimulated cell growth and concurrent cell genial selection. In turn, it is felt that decreasing such cell populations, especially of immune cells which trigger phagocytosis, would modify the course of autoimmune disease. Accordingly, pharmaceutical agents which depress leucocyte populations may be helpful in the treatment of autoimmune disease.

Deoxypyridoxine can be seen to be useful for the foregoing purposes. However, it produces a further decrease in vitamin $B_6$ deficiency when it is administered to animals receiving a $B_6$ deficient diet. This is undesirable since control of the $B_6$ level in such therapy should be possible.

Accordingly, it is an object of the invention to develop an immunosuppressive medicinal agent which does not adversely effect vitamin $B_6$ levels. Another object is the development of a highly active agent which does not necessitate administration of large doses in order to achieve the desired therapeutic effects.

SUMMARY OF THE INVENTION

These and other objects are achieved by the present invention which is directed to 2-acylimidazole compounds which exhibit immunosuppressive medicinal properties.

The 2-acylimidazole compounds of the invention are illustrated by Formula I:

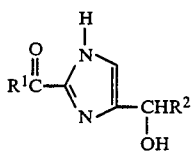

wherein $R^1$ is an alkyl of 1 to 4 carbons, phenyl, benzyl, or phenytethyl and $R^2$ is alkyl of 1 to 6 carbons, hydroxyalkyl of 1 to 6 carbons, polyhydroxyalkyl of 1 to 6 carbons having up to one hydroxyl per carbon, phenyl, benzyl, or phenylethyl.

Included within the compounds of Formula I are all enantiomers and optical isomer mixtures such as racemates, diastereomeric mixtures, unequal optical antipode mixtures. Furthermore, the imidazole ring exists as tautomers and both forms are included by Formula I.

Preferred compounds of Formula I are those having the following substituents: $R^1$ is alkyl; $R^2$ is hydroxyalkyl; $R^2$ is polyhydroxyalkyl; $R^2$ is hydroxyalkyl or polyhydroxyalkyl of 1 to 3 carbons; $R^2$ is 1,2,3-trihydroxypropyl, dihydroxypropyl, hydroxypropyl, dihydroxyethyl or hydroxymethyl; $R^1$ is methyl or ethyl; $R^1$ is phenyl, benzyl or phenylethyl and combinations of these preferred substituents.

Especially preferred compounds of formula I are those wherein;
1. $R^1$ is methyl and $R^2$ is 1,2,3-trihydroxypropyl;
2. $R^1$ is methyl and $R^2$ is 1,2-dihydroxyethyl;
3. $R^1$ is methyl and $R^2$ is hydroxymethyl;
4. $R^1$ is phenyl and $R^2$ is 1,2,3-trihydroxypropyl;
5. $R^1$ is phenyl and $R^2$ is 1,2-dihydroxyethyl;
6. $R^1$ is phenyl and $R^2$ is hydroxymethyl.

The invention is also directed to a method for isolating a compound of Formula I from a synthetic mixture containing it. This method utilizes a combination of two consecutive solid-phase complexations and a partition chromatography to isolate the compound. They are in order: treatment with a weakly acidic cation-exchange resin and water to produce a first aqueous phase and first solid phase, treatment of the first aqueous phase with a strongly acidic cation exchange resin and water to produce a second aqueous phase and a second solid phase, treatment of the second solid phase with dilute aqueous mineral acid to produce an acidic solution and chromatographing the acidic solution on a reverse phase immobilized $C_{14}$ to $C_{20}$ alkanoic acid solid phase using a dilute acid eluant. The preferred embodiments for the ion exchange steps are chromatographing with columns of ion-exchange resin.

The invention is further directed to methods for the suppression of transplanted tissue rejection, leukemic cell population reduction and treatment of cell-mediated autoimmune disease. These methods employ administration of a therapeutically effective amount of a 2-acylimidazole compound of the invention which is coupled with a control of the vitamin $B_6$ blood level so that it is slightly decreased below a normal value.

DETAILED DESCRIPTION OF THE INVENTION

The 2-acylimidazole compounds of the invention show a surprising ability to lower the population of lymphocytes in vivo. Since lymphocytes function in the immune response mechanism, a decrease in their numbers will lessen the biological response manifested by their action. It has been found that control of the vitamin $B_6$ level is necessary in order to achieve this effect; however, the administration of a compound of the invention does not cause further reduction of the $B_6$ level. Accordingly, the $B_6$ level can be adjusted to a slightly deficient value and controlled so that other vitamin $B_6$ deficiency effects do not occur.

The compounds can be synthesized by a "Maillard" (browning) reaction of ammonia, a pyruvaldehyde derivative of the formula $R^1COCHO$ and a hydroxyamine compound of the formula $$R^2CHOHCH(NH_2)CH_2OH$$

wherein $R^1$ and $R^2$ are defined as given above. This synthesis is shown by reaction 1 below.

The pyruvaldehyde derivatives and hydroxyamine compounds are generally known. The pyruvaldehyde derivatives may be prepared from the corresponding olefins by dihydroxylation with an agent such as periodate followed by mild oxidation. The hydroxyamine derivative may be prepared by amination of the corresponding 2-carbonyl alkose derivative.

Reaction 1

$$R^1COCHO + R^2CHOHCH(NH_2)CH_2OH + NH_3 \longrightarrow$$

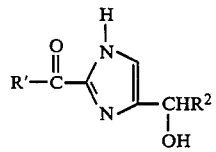

The preparation of the compounds of the invention by the "Maillard" reaction will typically be conducted in hot, polar hydroxylic solvent. The pyruvaldehyde derivative and hydroxyamine compound may be in a stoichiometric ratio with an excess of ammonia being used, but it is preferred to use an excess of the pyruvaldehyde derivative also. Usual practise will entail reacting the starting materials in refluxing aqueous solution while bubbling ammonia therethrough. After the reaction is complete, usually 2 to 15 hours, the reaction solution may be concentrated by evaporation of the solvent in vacuo. The product may then be isolated according to the isolation method described as follows.

Generally, the isolation is performed by successive treatment of the reaction mixture with a weak acid ion exchange resin such as carboxylic acid terminus resin, followed by treatment with a strong acid ion exchange resin such as sulfonic acid terminus resin. The acylimidazole compound will not bind to the weak acid resin but will bind to the strong acid resin when applied in aqueous solution. Consequently, the acylimidazole compound will be found in the aqueous phase of the first treatment and in the solid phase of the second treatment. Typically, these treatments are handled as chromatographies by eluting the exchange columns with water. Washing the second resin with a dilute aqueous mineral acid will cause release of the desired acylimidazole compound.

The final step is chromatography on a reverse phase $C_{14}$ to $C_{20}$ immobilized alkanoic acid column such as steric acid bound to silica. Elution of the column with dilute aqueous mineral acid provides an acidic aqueous solution of the acylimidazole compound which will crystallize therefrom upon standing. Treatment of this aqueous solution within alcohol such as ethanol will cause facile precipitation.

The compounds of the invention are medicinal agents which are useful as a result of their immunosuppressive activity. In general, the compounds of the invention act to lower in vivo leucocyte populations in mammals. Their effect upon the lymphocyte population indicates that they can be used for the treatment of immune response related maladies and malconditions. Accordingly, they are similar in activity to 4-deoxypyridoxine but it has been found that they do not cause a further lowering of the vitamin $B_6$ level when used according to a $B_6$ deficient regimen.

The compounds of the invention exhibit suppression of lymphocyte blood levels of rats which have been maintained upon a diet slightly deficient in vitamin $B_6$. Such tests have been correlated with an ability of the administered compounds to suppress or prevent transplanted tissue rejection. Moreover, they have been correlated with immune suppression in primates.

The compounds of the invention can be administered by any desired and appropriate route which will deliver therapeutic blood levels of the compounds. These routes would include oral, intravenous, intraperitoneal, rectal, intramuscular routes as well as others.

The compounds may be administered alone or in combination with suitable pharmaceutical carriers and with appropriate fomulations providing sterility, isotonicity and absorptive properties. Such carriers would include isotonic agents, absorptive agents, extenders, diluents, saline, gelling agents, surfactants, enteric coatings, milk sugars, starches, gums, pH adjusting agents and the like.

Dosage forms will be those appropriate for the route of administration. These include tablets, capsules, troches, elixirs, sterile aqueous or alcohol solutions, suspensions in emulsifying agents, suppositories in low melting waxes and the like.

It will be recognized that administration and dosage of the compounds of the invention will depend in large part upon the patient's unique conditions, his particular medical problem and upon the judgment of his attending physician. In general, the physician will balance these factors and determine the ultimate course of therapy. The dosage guidelines herein provided will suggest appropriate points for consideration when determining such therapy.

It will, therefore, be useful to administer the compounds in divided small doses and follow the blood levels of the compounds so that a threshold therapeutic dose can be achieved. This will be coupled with the production of a slight vitamin $B_6$ deficiency in the patient. This may be induced through use of a $B_6$ deficient diet or through use of $B_6$ antagonist such as linatine, agaritine, isonicotinic hydrazide, 4-deoxypyridoxine and the like. Typically, blood levels can be followed so that a level of about 0.25 mg per kg per day of compound is achieved with a $B_6$ level of about 50 to 75 percent of normal. Higher levels can then be employed until the appropriate sustained immunosuppressive effect is produced. This can be determined by a blood work up of WBC's which will indicate the suppressive effect. Dose levels can be adjusted until the desired level of WBC population suppression is achieved. Typically, a two to four-fold decrease in WBC levels may be appropriate.

The invention will be further illustrated by the following examples and biological studies. All temperatures are in degrees Celcius. The NMR spectral absorptions are in delta ppm relative to tetramethylsilane; C-13 and proton NMR spectra are indicated. Only significant peaks are noted. IR spectra are in reciprocal cm. Ultraviolet spectra are given in lambda max. Biological studies with rats were conducted with negative controls, i.e., control rats subjected to the conditions of the experiment but not dosed with compound.

EXAMPLE

Preparation of 2-Acetyl-4(5)-Tetrahydroxybutylimidazole (THAI)

A. Method of Synthesis and Purification

THAI was prepared by reacting fructosamine acetate (prepared according to the procedure given in "Methods of Carbohydrate Chemistry," Vol. 2, pp. 99–103 (1963), 23.9 g. 0.1 ml), pyruvaldehyde (40% aqueous solution, 20 ml) and excess ammonia. The fructosamine was dissolved in water (125 ml). Aqueous ammonia (28–30%, 1000 ml) was added, then the aqueous pyruvaldehyde. The mixture was heated under reflux for two hours while a slow stream of ammonia gas was bubbled through it. The light brown solution was cooled to room temperature, then concentrated in vacuo to a syrup, about 100 ml. The syrup was redissolved in water to give a volume of 300 ml and the pH was adjusted from 6.3 to 5.0 using hydrochloric acid.

THAI was isolated from the diluted syrup by chromatographing it a sequence of preparative weak and strong acidic cation exchange resins.

The diluted syrup was charged on a preparative, weakly acidic cation-exchanger Amberlite AG CG-50 (Rohm and Haas trademark for carboxylic acid terminus exchange resin) (100–200 mesh), which as connected in series with a second column filled with a strongly acidic cation-exchanger, Dowex AG 50 W×12 (Dow Chemical Co. trademark for sulfonic acid terminus exchange resin). The columns were (minus 400 mesh) eluted with water at a flux of about 25 ml per minute. After passage of about 3 l of water, practically all color had been transferred to the second column (Dowex). The Amberlite column was disconnected and elution of the Dowex column continued with water at a flux of approximately 25 ml/min until a total of 70 to 75 l had been passed through. Effluents were monitored with a detector: (Pharmacia UV-2, 1 mm cell, 20 AUFS, transmission mode), at 254 nm.

The desired product was recovered by elution of the Dowex exchanger with 0.5 M hydrochloric acid at a flux of 15 to 20 ml per min. 500 ml fractions were collected. Aliquots of these fractions were evaporated and analyzed by HPLC (RF-18, 10u, 250 by 4.6 min., 2 ml/min. 0.05 m phosphoric acid pH 2, detection at 214 and 280 nm). THAI (retention 2.3 min.) usually was found in fractions 10 and/or 11. These were evaporated to a syrup, redissolved in water (20 ml) and chromatographed on a column filled with Lichroprep RP-18 with 0.01 M-HCl as the eluent. Lichroprep is a reverse phase chromatographic material composed of steric acid bound to silica gel. The fractions producing an ultraviolet absorption peak (280 nm) corresponding to THAI were collected and the solution concentrated in vacuo to a colorless syrup which showed a tendency to crystallize slowly.

The syrup was dissolved in water (300 μl) and 5 M hydrochloric acid added (50 μl). The acid solution was treated with absolute ethanol (0.5 ml) and solution cooled in the refrigerator for a few days to produce near colorless crystals of THAI hydrochloride. Ether was added portionwise to the mother liquor with intermittent cooling to produce another crop. The total yield of THAI was about 110 mg.

The product THAI, had the following physical characteristics.

2-Acetyl-4(5)-tetrahydroxybutylimidazole (THAI)

UV: 276 nm (pH 2), 288 nm (pH 5), 309 nm (pH 11).
IR: 3360 (S), 2930 (S), 1705 (S), 1625 (M), 1490 (M), 1405 (S), 1365 (M), 1325 (W), 1215 (M), 1075 (S), 1030 (S), 880 (W), 790 (W), 630 (W), 540 (W).
$^{13}$C-NMR (D$_2$O, pH 2, 306 K): 186.4 S, 140.5 S, 139.0 S, 120.3 D, 73.6 D, 71.5 D, 65.9 D, 63.7 T, 27.0.Q.
MS:

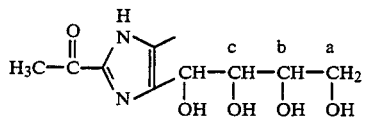

FAB: MW 230.08870, C$_9$H$_{14}$N$_2$O$_5$

Major fragments are formed by loss of one or two molecules of water, one molecule of ketene, and cleavage at a, b and c.

BIOLOGICAL STUDIES

SHORT-TERM (7-DAY) BIOASSAY IN RATS WITH THREE DOSE LEVELS OF THAI

Pure THAI synthesized as described above, was tested for lymphocyte population reducing activity in a 7-day bioassay in rats. The compound as administered to rats in the drinking water at levels of 2, 5 or 20 ppm.

1. Procedure

Treatment groups

The assay included four groups: three test groups, and one negative control group (demineralised water). The groups were coded as follows:
A control
B—2 ppm THAI
C—5 ppm THAI
D—20 ppm THAI Conduct Each group contained ten young male rats (Cpb:WU; Wistar random), bred under SPF conditions at the Central Institute for the Breeding of Laboratory Animals TNO, Zeist, The Netherlands.

Their ages were approximately 30 days, their weights were in a range of 75-100 g. They were housed in groups of 5 in screen-bottomed cages, under conventional conditions in an animal room which was controlled with respect to temperature (23°±1° C.), humidity (50±10%), ventilation (10 air changes/hour) and lighting (12 hours/day). During an acclimatization period of five days, the rats were provided ad libitum with "CIVO" rat basal diet for one day and then with semipurified basal diet deficient in pyridoxine for four days. Tap water was freely available during this period.

At the initiation of the assay period, the animals were allocated to the different groups in such a way that the average number of leucocytes of each group was approximately the same.

All animals were fed a semi-purified casein diet, deficient in pyridoxine. Upon analysis the vitamin B$_6$ content of the diet was found to be 0.1 mg/kg air-dry matter.

The body weight of the individual rats was recorded on day 0 and 7. The food intake of each group of 5 rats in one cage was measured over days 0–7. Fluid intake of the 5 rats in one cage was recorded daily. Hemoglobin levels and counts of total and differential white blood cells were made on day 6 in samples of blood collected from the tip of the tail. On day 7 the rats were killed by decapitation and the weights of the following organs were recorded: kidneys, thymus, spleen and caecum (filled and empty).

2. Results

Body weight, food intake and food efficiency

Body weight gain, food intake and food efficiency did not show any obvious differences amongst the groups.

Liquid intake

There were no dose-related differences in liquid intake amongst the various groups.

Hematology

There was a considerable decrease in numbers of lymphocytes in all groups treated with THAI. Even with 2 ppm THAI in the drinking water, the decrease was considerable. Only a slight, though dose-related, further decrease in lymphocytes was noticeable upon increasing the dose level from 2 to 20 ppm. Neutrophil counts showed a dose-related increase in the groups given THAI. The differential counts showed the well-known shift from lymphocytes to neutrophils both in all groups receiving THAI. With THAI, the shift in lymphocyte/neutrophil ratio was considerable and clearly dose-related. The results are summarized in Table 1.

TABLE 1

|  | LYMPHO (N) | NEUTRO (N) | % LYMPHO (O/O) | % NEUTRO (O/O) |
|---|---|---|---|---|
| CONTROL | 13.2 | 1.3 | 90.4 | 8.8 |
| THAI 2 PPM | 5.6 | 1.9 | 73.2 | 25.6 |
| THAI 5 PPM | 5.2 | 2.5 | 67.2 | 31.8 |
| THAI 20 PPM | 4.5 | 3.5 | 56.4 | 42.5 |

N = 10$^3$ cells/mm$^3$

Hemoglobin levels were increased in a statistically significant way, in all test groups.

Relative organ weights

The only change in relative organ weight was a decrease in the relative weight of the thymus in the group treated with 20 ppm THAI. In the lower dose groups, thymus weights tended to be decreased. Because the differences with the controls were dose-related the phenomenon might be attributed to THAI.

There were no obvious differences in the relative weight of the kidneys, spleen or caecum amongst the various groups.

The results of the bioassay showed that the synthesized compound 2-acetyl-4(5)-tetrahydroxybutylimidazole (THAI), exerted a lymphocyte population depressing activity in the rat bioassay.

A second study was conducted with rats fed 2.5 ppm pyridoxine in the basal diet. The procedures and conduct of the study were the same as given above. The results after thirteen days are tabulated in Table 2 below.

TABLE 2

| | TOTAL WBC | LYMPHO (N) | NEUTRO (N) | % LYMPHO (O/O) | % NEUTRO (O/O) |
|---|---|---|---|---|---|
| CONTROL | 14.7 | 12.9 | 1.5 | 88.5 | 9.8 |
| THAI: | | | | | |
| 0.4 PPM | 14.4 | 11.6 | 2.5 | 80.7 | 17.2 |
| 1.0 PPM | 16.4 | 12.9 | 3.2 | 79.6 | 19.2 |
| 2.0 PPM | 12.2 | 8.9 | 3.2 | 72.9 | 26.2 |
| 4.0 PPM | 9.8 | 6.9 | 2.8 | 70.2 | 27.7 |
| 8.0 PPM | 8.6 | 5.6 | 2.9 | 64.8 | 33.3 |

$N = 10^3$ cells/mm$^3$

COMPARISON OF THE EFFECT OF DEOXYPYRIDOXINE IN THE RAT BIOASSAY WITH THE EFFECT OF THAI

1. Materials

Deoxypyridoxine HCl was obtained from ICN Pharmaceuticals, Cleveland, USA and was stored in a freezer.

Deoxypyridoxine (DOP) was tested at levels of 1, 2, 4, 8 and 20 ppm in the drinking water.

Before treatment of the rats, DOP was mixed with an appropriate amount of demineralized water to obtain the desired concentrations. The solutions obtained (3500 g each) were used as the drinking water for one group of rats for the whole test period of 7 days. After preparation, the solutions were transferred into plastic bottles and stored in a freezer. Every other day, one bottle for each group as thawed at room temperature overnight. Half of it served as the drinking water for one group of rats for one day. The other half was kept refrigerated for 24 hours and provided as the drinking water for the second day.

2. Procedure

Treatment groups

Five test groups and one negative control group (demineralized water only) were used. The groups were coded as follows:

A control
B DOP 1 ppm
C DOP 2 ppm
D DOP 4 ppm
E DOP 8 ppm
F DOP 20 ppm

All animals received a semi-purified diet, low in pyridoxine (2-3 ppm).

Conduct of the study

Each group consisted of 10 male rats (Wistar derived, SPF-bred), obtained from the Central Institute for the Breeding of Laboratory Animals TNO, Zeist, The Netherlands. Five animals were housed in one cage. After an acclimatization period of 3 days on semi-purified diet and tap water, the test solutions and the semi-purified diet were provided for the next 7 days. At the initiation of the test period, the animals were allocated to the different groups in such a way that the average leucocyte counts were approximately the same in all groups.

Body weight of the individual rats were recorded at day 0 and 7. The food intake (on a cage basis) was measured over days 0-7. Fluid intake (on a cage basis) was determined daily.

Hemoglobin levels and total and differential white blood cell counts of tailtip blood were recorded at day 6.

At day 7 the animals were ether-anaesthetized and bled to death by puncture of the aorta abdominalis. Blood was collected in tubes treated with EDTA for determination of pyridoxal phosphate (PLP) in the plasma, according to the method of Chabner and Livingstone (Anal. Biochem. 34(1970) 413).

3. Results

Body weights, food intake and food efficiency

Body weight gain, food consumption and food efficiency the groups receiving 8 and 20 ppm deoxypyridoxine were decreased relative to the controls.

Liquid intake

There was a slight decrease in liquid intake with 20 ppm deoxypyridoxine.

Hematology

There were dose-related decreases in counts of total white blood cells and lymphocytes both in the groups receiving deoxypyridoxine. However, dose levels higher than 4 ppm deoxypryidoxine did not further reduce the number of lymphoctyes. The decrease in lymphocytes was noticeable already with 1 ppm deoxypyridoxine. Neutrophil counts tended to be increased in the groups in almost every DOP-treated group. The results are summarized in Table 3.

TABLE 3

DOP STUDY, TOTAL AND DIFFERENTIAL WHITE BLOOD CELL COUNTS (WBC) AND CALCULATED NUMBERS OF LYMPHOCYTES AND NEUTROPHILS, RECORDED AT DAY 6.

| GROUP | | | N* WBC | N* LYMPHO | N* NEUTRO | % LYMPHO | % NEUTRO |
|---|---|---|---|---|---|---|---|
| CONTROL | A | MEAN | 15.1 | 13.6 | 1.4 | 89.9 | 9.3 |
| | | SEM | 0.9 | 0.9 | 0.2 | 1.5 | 1.2 |
| DOP | B | MEAN | 14.9 | 12.5 | 2.2 | 83.6 | 14.7 |
| | | SEM | 0.7 | 0.7 | 0.1 | 1.0 | 0.8 |
| | C | MEAN | 13.7 | 11.0 | 2.5 | 80.1 | 18.4 |
| | | SEM | 0.5 | 0.6 | 0.2 | 1.9 | 1.9 |
| | D | MEAN | 9.8 | 8.0 | 1.6 | 81.7 | 17.0 |
| | | SEM | 0.5 | 0.5 | 0.1 | 1.7 | 1.4 |
| | E | MEAN | 9.5 | 7.0 | 2.4 | 72.9 | 25.8 |
| | | SEM | 1.1 | 0.9 | 0.3 | 2.9 | 2.6 |
| | F | MEAN | 10.3 | 7.7 | 2.5 | 75.3 | 23.8 |

TABLE 3-continued

DOP STUDY, TOTAL AND DIFFERENTIAL WHITE BLOOD CELL COUNTS (WBC) AND CALCULATED NUMBERS OF LYMPHOCYTES AND NEUTROPHILS, RECORDED AT DAY 6.

| GROUP | N* WBC | N* LYMPHO | N* NEUTRO | % LYMPHO | % NEUTRO |
|---|---|---|---|---|---|
| SEM | 0.4 | 0.4 | 0.5 | 4.3 | 4.1 |

*$N = 10^3$ cells/mm$^3$

Pyridoxal phosphate (PLP)

With the 8 and 20 ppm DOP doses, Pyridoxal phosphate levels in plasma tended to be further decreased relative to the already decreased levels produced by the $B_6$ deficient diet.

At low dose levels (1, 2 and 4 ppm DOP) lymphocytes showed a linear decrease with increasing dose level.

From a comparison of the tests for DOP and THAI it appears that the two compounds have similar effects on the circulating lymphocyte population in rats. THAI appears to require a slightly deficient vitamin $B_6$ regimen but does not further decrease the $B_6$ level, while deoxypyridoxine appears to decrease further the available vitamin $B_6$ in the bloodstream.

What is claimed is:

1. A 2-acylimidazole compound having the formula

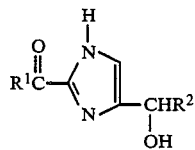

its enantiomers, tautomers, and mixtures of optical isomers, wherein:
 $R^1$ is an alkyl of 1 to 4 carbons, phenyl, benzyl, or phenylethyl; and
 $R^2$ is alkyl of 1 to 6 carbons, hydroxyalkyl of 1 to 6 carbons, polyhydroxyalkyl of 1 to 6 carbons having up to one hydroxyl per carbon, phenyl, benzyl, or phenylethyl.

2. A compound according to claim 1 wherein $R^1$ is alkyl and $R^2$ is alkyl, hydroxyalkyl or polyhydroxyalkyl.

3. A compound according to claim 1 wherein $R^2$ is hydroxyalkyl or polyhydroxyalkyl.

4. A compound according to claim 1 wherein $R^2$ is polyhydroxyalkyl.

5. A compound according to claim 4 wherein $R^1$ is alkyl.

6. A compound according to claim 5 wherein the polyhydroxyalkyl is 1 to 3 carbons in length.

7. A compound according to claim 5 wherein $R^2$ is 1,2,3-trihydroxypropyl.

8. A compound according to claim 5 wherein $R^2$ is 1,2-dihydroxypropyl.

9. A compound according to claim 5 wherein $R^2$ is 1,3-dihydroxypropyl.

10. A compound according to claim 5 wherein $R^2$ is dihydroxyethyl.

11. A compound according to claim 1 where $R^2$ is hydroxyalkyl.

12. A compound according to claim 11 wherein $R^1$ is alkyl.

13. A compound according to claim 12 wherein the hydroxyalkyl is 1 to 3 carbons in length.

14. A compound according to claim 12 wherein $R^2$ is hydroxypropyl.

15. A compound according to claim 12 wherein $R^2$ is hydroxymethyl.

16. A compound according to claim 12 wherein $R^2$ is hydroxyethyl.

17. A compound according to claim 1 wherein $R^1$ is phenyl, benzyl or phenylethyl.

18. A pharmaceutical composition for decreasing an in vivo lymphocytic population comprising a pharmaceutical carrier in combination with compound of claim 1.

19. A method for preventing cell mediated, transplanted tissue rejection in an animal having a tissue transplant comprising lowering the vitamin $B_6$ blood level in the animal and administering to the animal a therapeutic amount of a compound of claim 1.

20. A method for preventing or alleviating cell-mediated autoimmune disease in a patient with said disease comprising lowering the vitamin $B_6$ blood level in the patient and administering a therapeutic amount of a compound of claim 1.

21. A process for isolation of a 2-acylimidazole compound of the formula

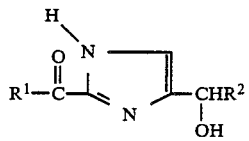

its enantiomers, tautomers and mixtures of optical isomers, wherein $R^1$ is an alkyl of 1 to 4 carbons, phenyl, benzyl or phenylethyl, and $R^2$ is alkyl of 1 to 6 carbons, hydroxyalkyl of 1 to 6 carbons having up to one hydroxyl per carbon, phenyl, benzyl, or phenylethyl from a mixture of reaction products from a synthetic reaction designed and conducted to produce the 2-acylimidazole compound, comprising:
 treating the mixture with a weakly-acidic cation-exchange resin and water to produce a first aqueous phase and a first solid phase;
 treating the first aqueous phase with a strongly acidic cation-exchange resin and water to produce a second aqueous phase and a second solid phase;
 treating the second solid phase with dilute aqueous mineral acid to produce an acidic solution; and
 chromatographing the acidic solution on a reverse phase immobilized $C_{14}$ to $C_{20}$ alkanoic acid solid phase using a dilute aqueous acid eluant to produce the isolated 2-acylimidazole compound.

22. A process according to claim 21 comprising using columns of weakly acidic and strongly acidic cation exchange resins and chromatographing the mixture and first aqueous phase through the respective columns.

23. A composition according to claim 18 wherein at least about 12.5 mg of the 2-acylimidazole compound is combined with the pharmaceutical carrier to provide a single dose of the composition.

24. A method according to claim 19, wherein the therapeutic amount is calculated to produce a blood level of the 2-acylimidazole compound of at least about 0.25 mg per kg patient weight per day.

25. A method according to claim 20 wherein the therapeutic amount is calculated to produce a blood level of 2-acylimidazole compound of at least about 0.25 mg per kg patient weight per day.

* * * * *

UNITED STATES PATENT AND TRADEMARK OFFICE
CERTIFICATE OF CORRECTION

PATENT NO. : 4,567,194
DATED : January 28, 1986
INVENTOR(S) : Kroeplien et al.

It is certified that error appears in the above—identified patent and that said Letters Patent is hereby corrected as shown below:

At column 2, line 37 please change "leucocye" to --leucocyte--.

At column 5, line 29 please change "famulations" to --formulations--.

At column 6, line 32 please change "it" to --in--.

At column 6, line 63 please change "steric acid" to --stearic acid--.

At column 7, line 38 please change "as" to --was--.

At column 10, line 35 please change "    effi-" to --    effi- --.
                                      ciency the         ciency of the At column 11, line 65 please change "where" to --wherein--.

At column 12, line 48 please change "carbons having" to --carbons,polyhydroxyalkyl of 1 to 6 carbons having--.

Signed and Sealed this

Nineteenth Day of August 1986

[SEAL]

Attest:

DONALD J. QUIGG

Attesting Officer

Commissioner of Patents and Trademarks